(12) United States Patent
Taylor et al.

(10) Patent No.: US 9,095,338 B2
(45) Date of Patent: Aug. 4, 2015

(54) SURGICAL STAPLE INSERTION DEVICE

(71) Applicant: SOLANA SURGICAL, LLC, Memphis, TN (US)

(72) Inventors: Alan G. Taylor, Memphis, TN (US); Rebecca H. Wahl, Escondido, CA (US); Ronald G. Litke, Sandy Hook, CT (US)

(73) Assignee: Wright Medical Technology, Inc., Memphis, TN (US)

( * ) Notice: Subject to any disclaimer, the term of this patent is extended or adjusted under 35 U.S.C. 154(b) by 243 days.

(21) Appl. No.: 13/731,842

(22) Filed: Dec. 31, 2012

(65) Prior Publication Data

US 2014/0097228 A1  Apr. 10, 2014

Related U.S. Application Data

(60) Provisional application No. 61/711,479, filed on Oct. 9, 2012.

(51) Int. Cl.
*A61B 17/068* (2006.01)
*A61B 17/064* (2006.01)
*A61B 17/80* (2006.01)
(Continued)

(52) U.S. Cl.
CPC ........... *A61B 17/068* (2013.01); *A61B 17/0642* (2013.01); *A61B 17/0682* (2013.01); *A61B 17/80* (2013.01); *A61B 2017/00862* (2013.01);
(Continued)

(58) Field of Classification Search
CPC ............. A61B 17/068; A61B 17/0642; A61B 17/0682; A61B 2017/00867
USPC .................. 227/175.1, 19, 181.1; 606/219
See application file for complete search history.

(56) References Cited

U.S. PATENT DOCUMENTS

| 5,478,354 | A | 12/1995 | Tovey |
| 5,882,351 | A | 3/1999 | Fox |

(Continued)

FOREIGN PATENT DOCUMENTS

| EP | 0552109 A1 | 7/1993 | |
| EP | 826340 A2 * | 3/1998 | ........... A61B 17/068 |

(Continued)

OTHER PUBLICATIONS

The International Search Report and Written Opinion of the International Searching Authority for PCT/US2013/063997, Apr. 7, 2014, Solana Surgical LLC (related to the present application).

(Continued)

*Primary Examiner* — Michelle Lopez
(74) *Attorney, Agent, or Firm* — Duane Morris LLP

(57) ABSTRACT

A staple inserter (12) for use with a surgical staple (10) during a surgical procedure, the surgical staple (10) including a middle section (14) and two side sections (16) that cantilever away from the middle section (14), the surgical staple (10) being selectively movable between a relaxed configuration and an opened configuration, the staple inserter (12) comprising a staple holder assembly (20) that is rotatable in a first direction relative to the surgical staple (10) to selectively engage and retain the surgical staple (10). The staple holder assembly (20) includes (i) a first engagement member (32) that is rotatable in the first direction relative to the surgical staple (10) to selectively engage and retain the surgical staple (10), and (ii) a second engagement member (32) that is rotatable in the first direction relative to the surgical staple (10) to selectively engage and retain the surgical staple (10).

22 Claims, 4 Drawing Sheets

(51) Int. Cl.
*A61B 17/00* (2006.01)
*A61B 19/00* (2006.01)

(52) U.S. Cl.
CPC . *A61B 2017/0645* (2013.01); *A61B 2019/4836* (2013.01)

(56) References Cited

U.S. PATENT DOCUMENTS

| | | |
|---|---|---|
| 5,990,382 A | 11/1999 | Fox |
| 6,018,094 A | 1/2000 | Fox |
| 6,071,284 A | 6/2000 | Fox |
| 6,287,310 B1 | 9/2001 | Fox |
| 6,325,806 B1 | 12/2001 | Fox |
| 7,240,677 B2 | 7/2007 | Fox |
| D574,498 S | 8/2008 | Fox et al. |
| D574,956 S | 8/2008 | Grim |
| D586,915 S | 2/2009 | Grim |
| 8,137,351 B2 | 3/2012 | Prandi |
| D669,984 S | 10/2012 | Cheney et al. |
| D669,985 S | 10/2012 | Cheney et al. |
| 2010/0237128 A1 | 9/2010 | Miller |

FOREIGN PATENT DOCUMENTS

| | | |
|---|---|---|
| FR | 2868938 A1 | 10/2005 |
| WO | WO2009135022 A1 | 11/2009 |

OTHER PUBLICATIONS

Invitation to Pay Additional Fees from the International Searching Authority, Jan. 23, 2014, for Application No. PCT/US2013/063997 (related application).

BioMedical Enterprises, Inc. Webpage: http://www.bme-tx.com/products/details/speed/, Staple Fixation "Speed" Product Description, Date of first disclosure not known by Applicant; however, the Applicant acknowledges that the product was on sale prior to the conception of the present invention, BioMedical Enterprises, Inc., San Antonio, TX.

International Bureau of WIPO, PCT International Preliminary Report on Patentability regarding corresponding PCT Application No. PCT/US2013/063997 issued Apr. 23, 2015, pp. 1-11.

* cited by examiner

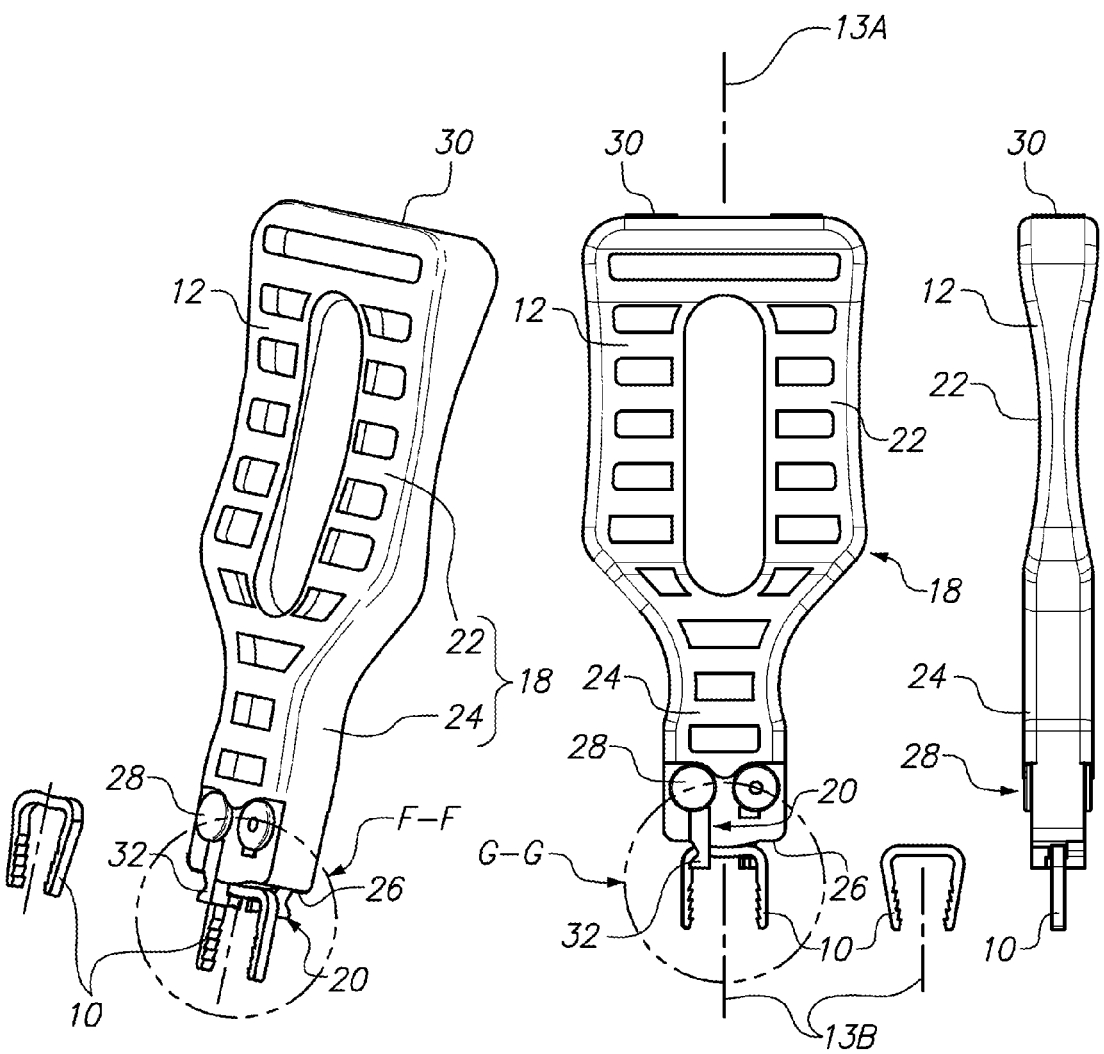
FIG. 1A  FIG. 1B  FIG. 1C

SURGICAL STAPLE INSERTION DEVICE

RELATED APPLICATION

The application claims priority on Provisional Application Ser. No. 61/711,479 filed on Oct. 9, 2012, entitled "SURGICAL STAPLE INSERTON DEVICE". As far as is permitted, the contents of U.S. Provisional Application Ser. No. 61/711,479 are incorporated herein by reference.

BACKGROUND

A surgical staple inserter device (also referred to herein as a "staple inserter") is used to retain a surgical staple during insertion of the surgical staple into the body, e.g., into certain bone material in the body. Surgical staples are often utilized for closure of the skin in a wide variety of surgical procedures. Additionally, surgical staples can be utilized to move and/or maintain bones or bone parts substantially adjacent to one another after certain surgical procedures. Moreover, surgical staples are often utilized to compress and hold together in place two displaced pieces of bone while healing. Often a hole or holes are necessary in the bone material for proper insertion of the surgical staples. During such insertion of the surgical staple, it is important that the staple inserter is able to retain the surgical staple securely to ensure that the surgical staple can be inserted accurately and precisely. Further, it is desired that the staple inserter can be quickly and easily removed after insertion of the surgical staple, without inhibiting or otherwise negatively impacting the proper positioning of the surgical staple.

SUMMARY

The present invention is directed to a staple inserter for use with a surgical staple during a surgical procedure, the surgical staple including a middle section and two side sections that cantilever away from the middle section, the surgical staple being selectively movable between a relaxed configuration and an opened configuration. In certain embodiments, the staple inserter comprises a staple holder assembly that is rotatable in a first direction relative to the surgical staple to selectively engage and retain the surgical staple.

With the design as illustrated and described herein, the staple inserter is able to securely retain the surgical staple during insertion of the surgical staple to ensure that the surgical staple can be inserted accurately and precisely. Additionally, with the present design, after insertion of the surgical staple, the staple inserter can be quickly and easily removed and/or moved away from the surgical staple without inhibiting or otherwise negatively impacting the proper positioning of the surgical staple.

In some embodiments, the staple holder assembly includes (i) a first engagement member that is rotatable in the first direction relative to the surgical staple to selectively engage and retain the surgical staple, and (ii) a second engagement member that is rotatable in the first direction relative to the surgical staple to selectively engage and retain the surgical staple. In one such embodiment, the first engagement member engages one of the side sections of the surgical staple, and the second engagement member engages the other side section of the surgical staple. Additionally, in such embodiment, the staple inserter can further comprise an inserter body, wherein the staple holder assembly is coupled to the inserter body, and wherein the inserter body includes an end that engages the middle section of the surgical staple when the engagement members are engaging the side sections of the surgical staple. In another such embodiment, each of the first engagement and the second engagement member engage the middle section of the surgical staple. Additionally, in such embodiment, the staple inserter can further comprise an inserter body, wherein the staple holder assembly is coupled to the inserter body, and wherein the inserter body includes an end that engages the middle section of the surgical staple when the engagement members are engaging the middle section of the surgical staple.

Additionally, in one embodiment, the staple holder assembly is rotatable relative to the surgical staple about a staple axis to selectively engage and retain the surgical staple, the staple axis being substantially parallel to the side sections when the surgical staple is in the opened configuration.

During use, in certain embodiments, when the staple holder assembly is engaging the surgical staple, the surgical staple is retained in the opened configuration, and when the staple holder assembly is not engaging the surgical staple, the surgical staple is in the relaxed configuration.

In some embodiments, the staple inserter further comprises an inserter body, wherein the staple holder assembly is coupled to the inserter body. In one such embodiment, the staple holder assembly is made from a metallic material and the inserter body is made from a plastic material.

Additionally, in some embodiments, the staple holder assembly is rotatable in a second direction relative to the surgical staple to disengage from the surgical staple, the second direction being opposite from the first direction.

The present invention is further directed to a combination comprising (i) a surgical staple including a middle section and two side sections that cantilever away from the middle section, the surgical staple being selectively movable between a relaxed configuration and an opened configuration, and (ii) the staple inserter as described above that selectively engages and retains the surgical staple.

Additionally, the present invention is also directed to a method for engaging and retaining a surgical staple during a surgical procedure, the surgical staple including a middle section and two side sections that cantilever away from the middle section, the surgical staple being selectively movable between a relaxed configuration and an opened configuration, the method comprising the step of rotating a staple holder assembly in a first direction relative to the surgical staple to selectively engage and retain the surgical staple.

Further, the present invention is also directed to a staple inserter for use with a surgical staple during a surgical procedure, the surgical staple including a middle section and two side sections that cantilever away from the middle section, the surgical staple being selectively movable between a relaxed configuration and an opened configuration, the staple inserter comprising (i) a first inserter member that selectively engages the surgical staple when the surgical staple is in the opened configuration, the first inserter member being made from a metallic material; and (ii) a second inserter member that is coupled to the first inserter member, the second inserter member selectively engaging the surgical staple when the surgical staple is in the opened configuration, the second inserter member being made from a plastic material.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIGS. 1A-1G are alternative views of a surgical staple and an embodiment of a staple inserter having features of the present invention, the staple inserter including an inserter body and a staple holder assembly;

DESCRIPTION

Figure 1D:
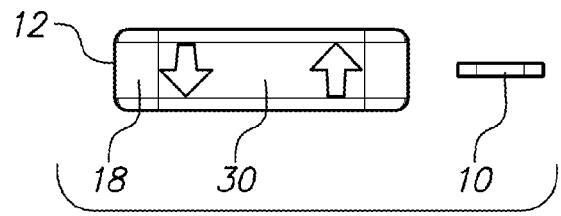
Figure 1F:
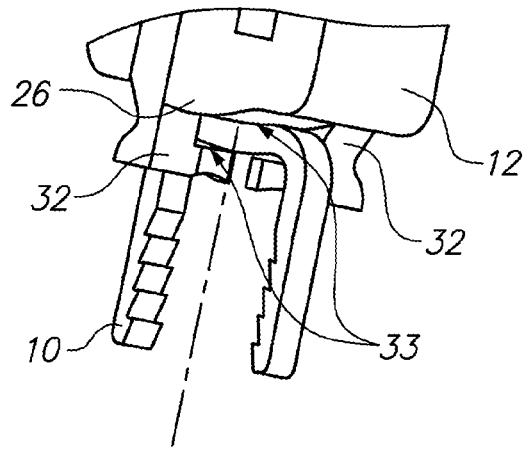
Figure 1E:
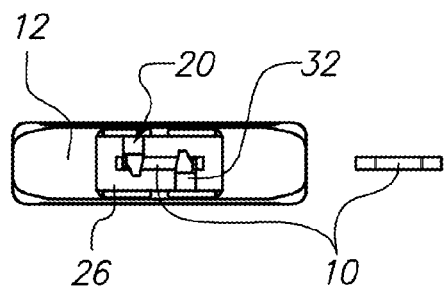
Figure 1G:
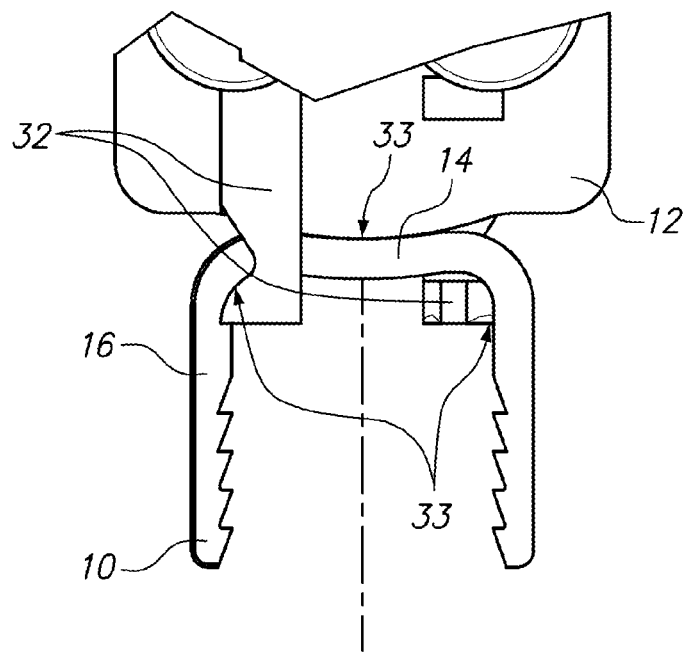

FIGS. 1A-1G are alternative views of a surgical staple 10 and an embodiment of a staple inserter 12 having features of the present invention. In particular, FIG. 1A is a perspective view of the surgical staple 10 and the staple inserter 12; FIG. 1B is a front view of the surgical staple 10 and the staple inserter 12; FIG. 1C is a side view of the surgical staple 10 and the staple inserter 12; FIG. 1D is a top view of the surgical staple 10 and the staple inserter 12; FIG. 1E is a bottom view of the surgical staple 10 and the staple inserter 12; FIG. 1F is an enlarged perspective view of the surgical staple 10 and a portion of the staple inserter 12 (as indicated by a circle and reference "F-F" in FIG. 1A); and FIG. 1G is an enlarged front view of the surgical staple 10 and a portion of the staple inserter 12 (as indicated by a circle and reference "G-G" in FIG. 1B).

As provided herein, the surgical staple 10 can be effectively utilized (i) for closure of the skin in a wide variety of surgical procedures; (ii) to move and/or maintain bones or bone parts substantially adjacent to one another after certain surgical procedures; and/or (iii) to compress and hold together in place two displaced pieces of bone while healing. Additionally and/or alternatively, the surgical staple 10 can be utilized for other suitable purposes.

Additionally, as illustrated and described herein, the staple inserter 12 can be moved, e.g., rotated, relative to the surgical staple 10 between an attached (or engaged) position and a detached (or disengaged) position. Stated in another fashion, the staple inserter 12 can move, e.g., rotate, in a first direction relative to the surgical staple 10 to selectively engage and retain the surgical staple 10; and the staple inserter 12 can move, e.g., rotate, in a second direction relative to the surgical staple 10 to disengage from the surgical staple 10, the second direction being substantially opposite from the first direction. Moreover, in certain embodiments, the staple inserter 12 can be rotated about an axis, e.g., an inserter axis 13A (illustrated in FIG. 1B) and/or a staple axis 13B (illustrated in FIG. 1B). It should be noted that when the staple inserter 12 is in the attached position, the inserter axis 13A and the staple axis 13B can be parallel and/or substantially coaxial.

In particular, when in the attached position, the staple inserter 12 engages and holds the surgical staple 10 securely while the surgical staple 10 is being inserted for any of the procedures noted above, e.g., while the surgical staple 10 is being inserted across an osteotomy. After insertion of the surgical staple 10, the staple inserter 12 can then be quickly and easily detached from the surgical staple 10, e.g., by rotating the staple inserter 12 in the second direction relative to the surgical staple 10, such that the staple inserter 12 is moved to the detached position. Further, the staple inserter 12 can be designed such that, after detachment of the staple inserter 12, an end or another portion of the staple inserter 12 can be seated on top of the surgical staple 10 and can be used to tamp the surgical staple 10 completely into the bone.

It should be noted that in FIGS. 1A, 1B and 1E, one surgical staple 10 is illustrated being held by the staple inserter 12, i.e. with the staple inserter 12 in the attached (or engaged) position, and an additional surgical staple 10 is illustrated spaced apart from the staple inserter 12, i.e. with the staple inserter 12 in the detached (or disengaged) position. Additionally, in FIG. 1D, the surgical staple 10 is only illustrated in the detached (or disengaged) position, as a surgical staple 10 in the attached (or engaged) position would not be visible from the top view of the staple inserter 12.

Additionally, it should further be noted that in certain embodiments, as described herein below, when the surgical staple 10 is being held by the staple inserter 12, i.e. when the staple inserter 12 is in the attached (or engaged) position, the surgical staple 10 is in an opened configuration. Further, in such embodiments, when the surgical staple 10 is not being held by the staple inserter 12, i.e. when the staple inserter 12 is in the detached (or disengaged) position, the surgical staple 10 is in a relaxed configuration. Stated in another fashion, the surgical staple 10 is designed to have resilient properties such that the surgical staple 10 is biased to return and/or move toward the relaxed configuration. With this design, when the surgical staple 10 is being held by the staple inserter 12, the resilient nature of the surgical staple 10 helps to provide the necessary force between the surgical staple 10 and the staple inserter 12 to enable the staple inserter to securely and effectively hold and/or retain the surgical staple 10.

In certain embodiments, the surgical staple 10 is moved from the relaxed configuration to the opened configuration prior to the surgical staple 10 being engaged by the staple inserter 12. In such embodiments, any suitable method, e.g., manual, automatic, etc., can be utilized to move the surgical staple 10 from the relaxed configuration to the opened configuration. Additionally and/or alternatively, in one embodiment, the staple inserter 12 can be moved to selectively engage the surgical staple 10 in order to move the surgical staple 10 between the relaxed configuration and the opened configuration. It should be noted that regardless of how the surgical staple 10 is moved from the relaxed configuration to the opened configuration, the staple inserter 12 is effectively utilized to selectively engage the surgical staple 10 to maintain the surgical staple 10 in the opened configuration.

The design of the surgical staple 10 can be varied depending on the requirements of the procedure to be performed. As shown in FIGS. 1A-1G, the surgical staple 10 can be somewhat horseshoe shaped, and, as shown most clearly in FIG. 1G, the surgical staple 10 can include a substantially flat middle section 14 (also referred to as a "staple backspan") and two side sections 16 (also referred to as "staple legs") that cantilever away from the middle section 14.

Additionally, in this embodiment, when the surgical staple 10 is in the relaxed configuration, each of the side sections 16 can cantilever away from the middle section 14 at an interior angle (also referred to herein as a "leg angle") of less than ninety degrees such that the side sections 14 are angled slightly toward one another (for example, as shown in FIGS. 1A, 1B and 1E when the surgical staple 10 is not being held and/or is spaced apart from the staple inserter 12). For example, in one non-exclusive embodiment, when the surgical staple 10 is in the relaxed configuration, each of the side sections 16 cantilevers away from the middle section 14 at an interior angle of approximately eighty degrees. Alternatively, when the surgical staple 10 is in the relaxed configuration, each of the side sections 16 can cantilever away from the middle section 14 at an interior angle of approximately 85.0, 84.0, 83.0, 82.0, 81.0, 79.0, 78.0, 77.0, 76.0, or 75.0 degrees, or at some other interior angle. Additionally, in alternative embodiments, when the surgical staple 10 is in the relaxed configuration, each of the side sections 16 can cantilever away from the middle section 14 such that the interior angle between one side section 16 and the middle section 14 is substantially equal to the interior angle between the other side section 16 and the middle section, or the side sections 16 can cantilever away from the middle section 14 at different interior angles from one another.

Moreover, as noted above, the surgical staple 10 is designed to have resilient properties such that the surgical staple 10, i.e. the side sections 16 of the surgical staple 10 relative to the middle section 14, is biased to return and/or move toward the relaxed configuration.

Further, in this embodiment, when the surgical staple 10 is in the opened configuration, each of the side sections 16 can cantilever away from the middle section 14 at an interior angle of approximately ninety degrees, i.e. substantially perpendicularly (for example, as shown in FIGS. 1A, 1B, 1F and 1G when the surgical staple 10 is being held by the staple inserter 12). By holding and retaining the surgical staple 10 such that the side sections 16 cantilever away from the middle section at an interior angle of approximately ninety degrees, the surgical staple 10 can be quickly and easily inserted into the holes that have been created in the bones or bone parts to specifically receive the surgical staple 10. Alternatively, when the surgical staple 10 is in the opened configuration, each of the side sections 16 can cantilever away from the middle section 14 at an interior angle of approximately 95.0, 94.0, 93.0, 92.0, 91.0, 89.0, 88.0, 87.0, 86.0, or 85.0 degrees, or at some other interior angle.

It should be noted that, in certain embodiments, it is desirable that the difference of the interior angles between the side sections 16 and the middle section 14 in the relaxed configuration, and the interior angles between the side sections 16 and the middle section 14 in the opened configuration, be at least approximately 5.0 degrees so that the resilient properties of the surgical staple 10 are sufficient to enable the staple inserter to securely and effectively hold and/or retain the surgical staple 10. For example, in certain non-exclusive embodiments, the difference in such interior angles between the relaxed configuration and the opened configuration can be approximately 6.0, 8.0, 10.0, 12.0, 14.0, or 15.0 degrees, or some other interior angle difference.

Alternatively, the surgical staple 10 can be designed such that the interior angle of the side sections 16 relative to the middle section 14 does not change as the staple inserter 12 moves between the attached position and the detached position.

A suitable surgical staple 10 for use with the present invention can be found in U.S. Provisional Application Ser. No. 61/605,269, filed Mar. 1, 2012 and entitled "Surgical Staple"; and in U.S. Provisional Application Ser. No. 61/642,353, filed May 3, 2012 and entitled "Surgical Staple". As far as permitted, the contents of U.S. Provisional Application Ser. Nos. 61/605,269 and 61/642,353 are incorporated herein by reference.

The staple inserter 12 can be varied as necessary in design and size to be usable with a variety of different surgical staples 10 and/or to suit the design preferences of the user. In the embodiment illustrated in FIGS. 1A-1G, the staple inserter 12 includes an inserter body 18 and a staple holder assembly 20 that is secured to or otherwise coupled to the inserter body 18. It should be noted that the inserter body 18 and the staple holder assembly 20 can be alternatively referred to as a "first inserter member" and/or a "second inserter member".

In one embodiment, as illustrated, the inserter body 18 includes a first region 22 (or "main region") and a second region 24 (or "neck region") that extends away from the first region 22. As shown, the first region 22 can be somewhat rectangular block shaped and can include indented regions along the sides and/or along the faces of the first region 22 to enable the staple inserter 12 to be easily gripped during use. Additionally, as shown, the second region 24 can also be somewhat rectangular block shaped. Further, the second region 24 can be somewhat smaller than the first region 22 so that an end 26 of the second region 24 is somewhat similar to the general size, e.g., the width, of the surgical staple 10. With this design, the staple inserter 12 is less likely to interfere with the bone material during insertion of the surgical staple 10.

Further, the second region 24 can also include one or more features for securing the staple holder assembly 20 to the inserter body 18. For example, in one embodiment, the second region can include one or more recessed areas (not illustrated) or cavities, such that a portion of the staple holder assembly 20 can be positioned and securely retained within the recessed area. Additionally and/or alternatively, one or more coupling members 28 can further be provided to secure or otherwise couple the staple holder assembly 20 to the inserter body 18. The coupling members 28 can have any suitable design to enable the staple holder assembly 20 to be effectively and securely connected to the inserter body 18.

The size of the inserter body 18 can be varied to suit the comfort of the user and/or such that the inserter body 18 is suitable for use with specific sizes of surgical staples 10. Additionally, in certain embodiments, the inserter body 18 can be made from a plastic (e.g., polycarbonate) material, or another suitable material. Moreover, by utilizing such a plastic material to form the inserter body 18, certain frictional forces between the inserter body 18 and the surgical staple 10 may be inhibited during any contact between the inserter body 18 and the surgical staple 10, e.g., while the staple inserter 12 is being moved between the engaged position and the disengaged position.

Moreover, as illustrated in FIG. 1D, a top end 30 of the inserter body 18 can include arrows or other similar indicators to demonstrate the proper rotation of the staple inserter 12 (i.e. in the second direction) in order to detach the stapler inserter 12 from the surgical staple 10 after insertion of the surgical staple 10. Additionally and/or alternatively, the top end 30 can further include arrows or other similar indicators to demonstrate the proper rotation of the staple inserter 12 (i.e. in the first direction) in order to attach the staple inserter 12 to the surgical staple 10. Still alternatively, any such arrows or indicators can be included on another portion of the staple inserter 12.

As provided above, the staple holder assembly 20 is secured or otherwise coupled to the inserter body 18, with such securing or coupling being accomplished in any suitable manner. Additionally, the staple holder assembly 20 is designed to engage and retain the surgical staple 10 prior to and during insertion of the surgical staple 10. For example, in certain embodiments, the surgical staple 10 can be selectively moved from the relaxed configuration to the opened configuration, and then the staple holder assembly 20 is rotated, e.g., about the inserter axis 13A and/or the staple axis 13B, in the first direction to selectively engage and retain the surgical staple 10. As provided above, the surgical staple 10 can be moved from the relaxed configuration to the opened configuration in any suitable manner, prior to the staple inserter 12 selectively engaging the surgical staple 10 to maintain the surgical staple 10 in the opened configuration. Additionally and/or alternatively, in one embodiment, the staple holder assembly 20 itself can selectively engage the surgical staple 10 in order to move the surgical staple 10 between the relaxed configuration and the opened configuration.

It should be noted that, as utilized herein, the inserter axis 13A extends substantially parallel to a length of the inserter body 18 of the staple inserter 12. Additionally, it should be noted that, as utilized herein, the staple axis 13B extends substantially perpendicular to the middle section 14 of the surgical staple 10 and/or substantially parallel to the side sections 16 of the surgical staple 10 when the surgical staple 10 is in the opened configuration.

In one embodiment, the staple holder assembly 20 includes a pair of engagement members 32 that are each individually secured or otherwise coupled to the inserter body 18. Alternatively, the pair of engagement members 32 can be integrally formed with one another. Still alternatively, the staple holder assembly 20 can be designed with more than two engagement members 32 or the staple holder assembly 20 can include only a single engagement member 32.

During use, in the embodiment illustrated in FIGS. 1A-1G, each of the engagement members 32 is positioned and/or rotated in the first direction so as to selectively engage a different side section 16 of the surgical staple 10, i.e. the engagement members 32 are moved to the attached position. Additionally, one of the engagement members 32 selectively engages the surgical staple 10 from a front side of the surgical staple 10, and the other engagement member 32 selectively engages the surgical staple 10 from a back side (i.e. the opposite side) of the surgical staple 10. Stated in another fashion, one engagement member 32 is positioned and/or rotated in the first direction so as to selectively engage one of the side sections 16 from the front side of the surgical staple 10, and the other engagement member 32 is positioned and/or rotated in the first direction so as to selectively and simultaneously engage the other side section 16 of the surgical staple 10 from the back side (i.e. the opposite side) of the surgical staple 10. Moreover, each of the engagement members 32 can also engage the middle section 14 of the surgical staple 10 near the junction between the middle section 14 and the corresponding side section 16. Alternatively, in one embodiment, the engagement members 32 can be positioned such that one or both of the engagement members 32 only engage the middle section 14 of the surgical staple 10 near the junction between the middle section 14 and the corresponding side section 16, and the engagement members 32 do not engage the side sections 16.

Additionally, in one embodiment, while the engagement members 32 are engaging the surgical staple 10, the middle section 14 of the surgical staple 10 is further in contact with the end 26 of the inserter body 18, i.e. with the end 26 of the second region 24 of the inserter body 18. With this design, during use, there are three points of contact 33 (illustrated most clearly in FIG. 1G), or pressure points, between the surgical staple 10 and the staple inserter 12. As noted above, when the surgical staple 10 is in the relaxed configuration, each of the side sections 16 can cantilever away from the middle section 14 at an interior angle of less than ninety degrees such that the side sections 14 are angled slightly toward one another. With the three points of contact as discussed herein, the staple inserter 12 applies pressure at each of these three points of contact to effectively maintain the side sections 16 in the opened configuration such that the side sections 16 can be easily and accurately inserted into the holes in the bone material. Stated another way, the three points of contact between the staple inserter 12 and the surgical staple 10 when the staple inserter 12 is in the attached position enable the surgical staple 10 to be retained in the opened configuration. In particular, the pressure on the middle section 14 from the end 26 of the second region 24 of the inserter body 18 tends to maintain the side sections 16 slightly opened or spread apart relative to the relaxed configuration of the surgical staple 10; and the pressure of the engagement members 32 against an inner surface of the side sections 16 also tends to maintain the side sections 16 slightly opened or spread apart relative to the relaxed configuration of the surgical staple 10. In one embodiment, the side sections 16 can be maintained in such position with this method such that the side sections 16 are substantially perpendicular to the middle section 14 and/or such that the side sections 16 are substantially parallel to one another (for example, as shown in the Figures when the surgical staple 10 is being held by the staple inserter 12). This enables the side sections 16 to be more easily, accurately and precisely inserted into the holes in the bone material as desired.

After the surgical staple 10 has been inserted into the holes in the bone material (or otherwise inserted as desired), the staple inserter 12 can be rotated by rotating the inserter body 18 so that the staple holder assembly 20 (i.e. the engagement members 32) becomes disengaged from the surgical staple 10, i.e. so that the staple inserter 12 and/or the engagement members 32 are moved from the attached position to the detached position. At this point the staple inserter 12 can be moved away from the surgical staple 10. Further, in one embodiment, the ends or another portion of the staple inserter 12 can be scalloped to, once disengaged, seat on top of the surgical staple 10 and tamp the surgical staple 10 completely into the bone material.

The size and/or specific positioning of the engagement members 32 of the staple holder assembly 20 can be varied to suit the specific requirements of the surgical staples 10 being used. Moreover, in certain embodiments, the engagement members 32 are designed to be very thin such that the surgical staple 10 can be very close to its fully seated position when the staple inserter 12 is disengaged from the surgical staple 10. With this design, the full seating of the surgical staple 10 within the bone material can be relatively easy to accomplish.

Additionally, in certain embodiments, the staple holder assembly 20 can be made from stainless steel, another suitable metallic material that provides sufficient stiffness for the engagement members 32, or another suitable material, e.g., carbon fiber, which may also provide sufficient stiffness for the engagement members 32. Moreover, utilizing such materials for the engagement members 32 (for example, as opposed to using a plastic material similar to what may be used for the inserter body 18) enables the engagement members to be very thin so as to minimize the amount of movement necessary after the staple inserter 12 is disengaged from the surgical staple 10 to fully seat the surgical staple 10 within the bone material.

Figure 2A:
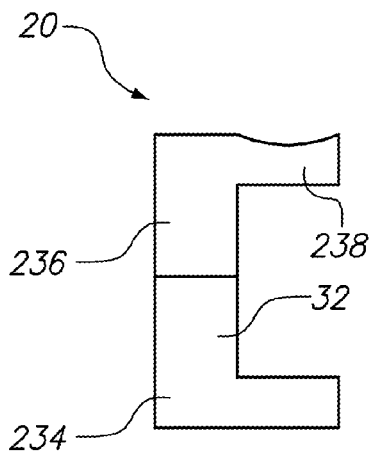
FIGS. 2A-2C are alternative views of a portion of the staple holder assembly illustrated in FIGS. 1A-1G.
Figure 2B:
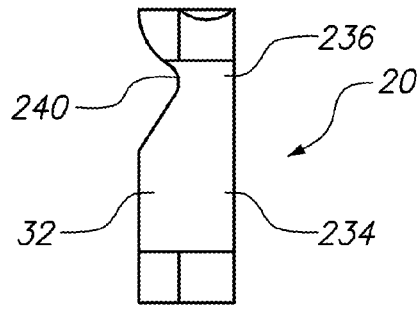
Figure 2C:
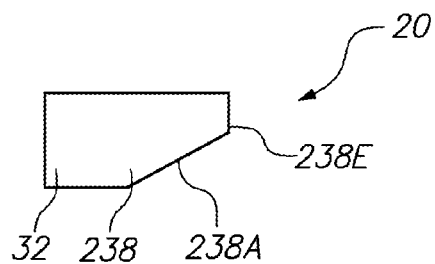

FIGS. 2A-2C are alternative views of a portion of the staple holder assembly 20 illustrated in FIGS. 1A-1G. In particular, FIG. 2A is a side view of one of the engagement members 32 of the staple holder assembly 20; FIG. 2B is a front view of the engagement member 32 illustrated in FIG. 2A; and FIG. 2C is a bottom view of the engagement member 32 illustrated in FIG. 2A.

The design of the engagement member 32 can be varied. As illustrated in FIG. 2A, in one embodiment, the engagement member 32 can include (i) a first section 234 (or "securing section") that can be positioned within one of the one or more recessed areas or cavities of the inserter body 18 (illustrated in FIG. 1A), or can be otherwise secured to the inserter body 18; and (ii) a second section 236 (or "cantilevering section") that cantilevers and/or extends away from the inserter body 18.

Additionally, the engagement member 32 can be formed from a single piece of material, and/or the engagement member 32 can include multiple pieces of material that have been secured or otherwise coupled together. In one embodiment, the engagement member 32 can be made from stainless steel. Alternatively, the engagement member 32 can be made from another suitable material, e.g., another metallic material.

The size and shape of the engagement member 32 can be varied as required to suit the specific requirements of the particular surgical staple 10 (illustrated in FIG. 1A) being used. For example, in one embodiment, from the side view perspective (as shown in FIG. 2A), the engagement member 32 can be substantially C-shaped. Alternatively, the engagement member 32 can have another shape.

In this embodiment, as shown in FIG. 2A, the second section 236 of the engagement member 32 includes a holder region 238 that is adapted to selectively engage the surgical staple 10 during insertion of the surgical staple 10. Stated in another fashion, as the engagement member 32 is rotated in the first direction into the attached position for use, the holder region 238 extends into and/or through the horseshoe shape of the surgical staple 10 so that the holder region 238 selectively engages the side section 16 (illustrated in FIG. 1G) and/or the middle section 14 (illustrated in FIG. 1G) of the surgical staple 10.

Additionally, in one embodiment, from the front view perspective (as shown in FIG. 2B), the engagement member 32 can be substantially rectangle shaped. Moreover, as shown, one or both of the first section 234 and the second section 236 of the engagement member 32 can include an angled and/or rounded indentation 240 that can be used to further enable and enhance the attachment and detachment procedures, i.e. when the staple inserter 12 (illustrated in FIG. 1A) is moved between the attached position and the detached position. In certain embodiments, one side of the indentation 240 can be angled at between approximately twenty-five and forty-five degrees relative to the side of the engagement member 32 from which the indentation 240 is formed. For example, in one non-exclusive embodiment, as illustrated in FIG. 2B, one side of the indentation 240 can be angled at approximately thirty-three degrees relative to the side of the engagement member 32 from which the indentation 240 is formed. Alternatively, such side of the indentation 240 can be angled at greater than forty-five degrees or less than twenty-five degrees relative to the side of the engagement member 32 from which the indentation 240 is formed.

Further, in one embodiment, from the bottom view perspective (as shown in FIG. 2C), the engagement member 32 is somewhat rectangle shaped, with an angled section cut away from one corner of the holder region 238 to create an angled portion 238A of the holder region 238. The angled portion 238A can be used to further enable and enhance the attachment and detachment procedures, i.e. when the staple inserter 12 is moved between the attached position and the detached position. For example, the presence of the angled portion 238A inhibits an end 238E of the holder region 238 from contacting the surgical staple 10 (illustrated in FIG. 1A) in an undesired manner during the attachment procedure, which may otherwise complicate and/or slow down the attachment procedure. In certain embodiments, the angled portion 238A of the holder region 238 may be cut at an angle of between approximately twenty and thirty-five degrees. For example, in one non-exclusive embodiment, as illustrated in FIG. 2C, the angled portion 238A of the holder region 238 may be cut at an angle of approximately twenty-eight degrees. Alternatively, the angled portion 238A of the holder region 238 may be cut at an angle of greater than thirty-five degrees or less than twenty degrees.

Moreover, FIGS. 2A-2C illustrate a design and shape of one specific, non-exclusive embodiment of the engagement member 32. Alternatively, the specific design and/or shape of the engagement member 32 can be varied from what is shown in the Figures, without deviating from the intended scope and breadth of the present invention.

Figure 3A:
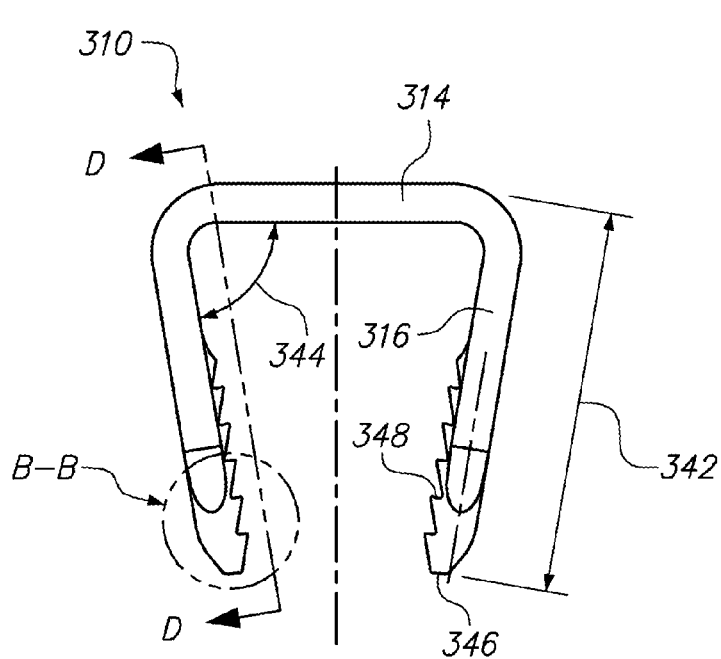
FIGS. 3A-3E are alternative views of an embodiment of a surgical staple that can be used in conjunction with the staple inserter illustrated in FIGS. 1A-1G.
Figure 3B:
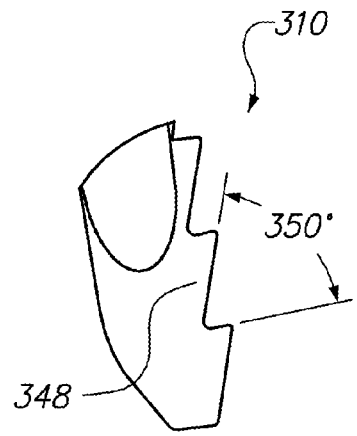
Figure 3C:
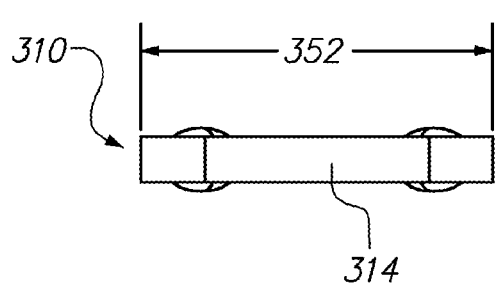
Figure 3D:
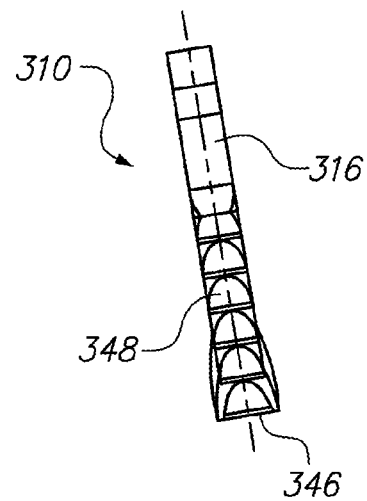
Figure 3E:
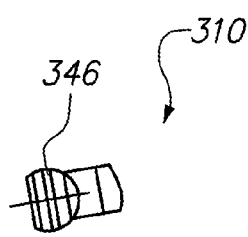

FIGS. 3A-3E are alternative views of an embodiment of a surgical staple 310 that can be used in conjunction with the staple inserter 12 illustrated in FIGS. 1A-1G. In particular, FIG. 3A is a front view of the surgical staple 310; FIG. 3B is an enlarged front view of a portion of the surgical staple 310 (as indicated by a circle and reference "B-B" in FIG. 3A); FIG. 3C is a top view of the surgical staple 310; FIG. 3D is a sectional view of the surgical staple 310 taken on line D-D in FIG. 3A; and FIG. 3E is a bottom view of a portion of the surgical staple 310. Moreover, it should be noted that the surgical staple 310 is illustrated in the relaxed configuration.

The design of the surgical staple 310 can be varied. As illustrated in FIG. 3A, in this embodiment, the surgical staple 310 can be somewhat horseshoe shaped, and the surgical staple 310 can include a substantially flat middle section 314 (also referred to as a "staple backspan") and two side sections 316 (also referred to as "staple legs") that cantilever away from the middle section 314.

As shown in FIG. 3A, the surgical staple 310 has a height 342 that is measured basically along the length of one (or each) of the side sections 316. In certain embodiments, the height 342 of the surgical staple 310 can be between approximately eight millimeters and twelve millimeters. For example, in a few non-exclusive alternative embodiments, the height 342 of the surgical staple 310 can be approximately 8.0, 9.0, 10.0, 11.0 or 12.0 millimeters. Alternatively, the height 342 of the surgical staple 310 can be greater than twelve millimeters or less than eight millimeters.

Additionally, as shown in the relaxed configuration, in this embodiment, each of the side sections 316 can cantilever away from the middle section 314 at a leg angle 344 of less than ninety degrees such that the side sections 316 are angled slightly toward one another. For example, in one non-exclusive embodiment, the side sections 316 can cantilever away from the middle section 314 at a leg angle 344 of approximately eighty degrees. Alternatively, the leg angle 344 between the side sections 316 and the middle section 314 can be greater than or less than eighty degrees. For example, in certain non-exclusive alternative embodiments, the leg angle between the side sections 316 and the middle section 314 can be approximately 85.0, 84.0, 83.0, 82.0, 81.0, 79.0, 78.0, 77.0, 76.0, or 75.0 degrees, or some other angle.

Further, as illustrated in FIG. 3A, each side section 316 has an end 346 that is somewhat tapered such that the end 346 is narrower in cross-section that the majority of the side section 316 to better enable insertion of the surgical staple 310.

Still further, in some embodiments, the side sections 316 of the surgical staple 310 can include a plurality of teeth 348 that are angled so as to enable easy insertion of the surgical staple 310, while inhibiting removal of the surgical staple 310. In certain embodiments, the surgical staple 310 can include between three and six teeth 348 along each of the side sections 316. Alternatively, each side section 316 can include greater than six or less than three teeth 348.

As noted above, FIG. 3B is an enlarged view of a portion of the surgical staple 310 illustrated in FIG. 3A. As shown in FIG. 3B, each tooth 348 can have a tooth angle 350 of approximately seventy degrees. Alternatively, each tooth 348 can have a tooth angle 350 of greater than or less than seventy degrees.

FIG. 3C provides a top view of the surgical staple 310, which illustrates a width 352 of the surgical staple 310, which is measured basically along the length of the middle section 314 of the surgical staple 310. In certain embodiments, the width 352 of the surgical staple 310 can be between approximately eight millimeters and twelve millimeters. For example, in a few non-exclusive alternative embodiments, the width 352 of the surgical staple 310 can be approximately 8.0, 9.0, 10.0, 11.0 or 12.0 millimeters. Alternatively, the width 352 of the surgical staple 310 can be greater than twelve millimeters or less than eight millimeters.

With the design of the surgical staple 310 as illustrated and described herein, the surgical staple 310 can achieve certain desired benefits. For example, the staple legs 316 have a wider foot design such that (i) the staple leg 316 fills the distal hole more completely; (ii) the larger area means better force distribution against the bone; (iii) better force distribution means better bone to bone compression because the staple leg 316 can move the bones together more effectively rather than just cutting into bone; and (iv) better filling of the hole means more distance the staple leg 316 can move the bone so as to enable better compression.

In one embodiment, the surgical staple 310 can be formed from a nitinol superelastic material. Alternatively, the surgical staple 310 can be made from another appropriately flexible and/or elastic material.

Further, as illustrated, the surgical staple 310 can have a unitary construction such that the surgical staple 310 is formed from a single piece of nitinol superelastic material, or other appropriate material. With this design, the connections between the middle section 314 and each of the side sections 316 can be somewhat rounded. Alternatively, the surgical staple 310 can be made of individual sections that are secured together.

Figure 4:
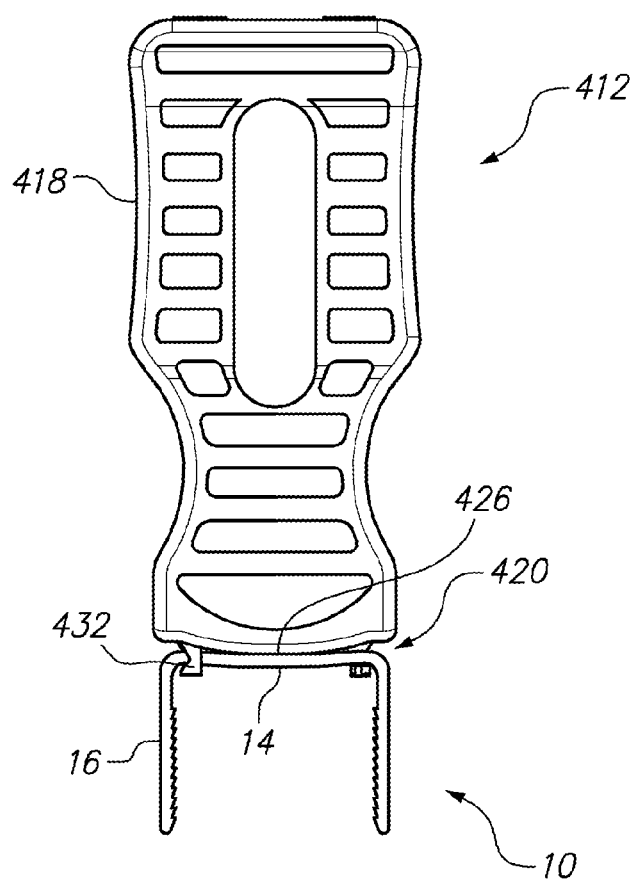
FIG. 4 is a front view of the surgical staple and another embodiment of a staple inserter having features of the present invention.

FIG. 4 is a front view of the surgical staple 10 and another embodiment of a staple inserter 412 having features of the present invention. The staple inserter 412 illustrated in FIG. 4 is substantially similar to the staple inserter 12 illustrated and described above. For example, the staple inserter 412 includes an inserter body 418 and a staple holder assembly 420 that are substantially similar to the inserter body 18 and the staple holder assembly 20 illustrated and described above. Moreover, the staple holder assembly 420 is again secured or otherwise coupled to the inserter body 418, and the staple holder assembly 420 again includes a pair of engagement members 432 that are secured or otherwise coupled to the inserter body 418.

However, in the embodiment illustrated in FIG. 4, during use, each of the engagement members 432 is positioned and/or rotated in the first direction so as to selectively engage a different portion of the middle section 14 of the surgical staple 10. For example, in one embodiment, one of the engagement members 432 is positioned and/or rotated in the first direction to selectively engage the middle section 14 of the surgical staple 10 near one of the side sections 16, and the other engagement member 432 is positioned and/or rotated in the first direction to selectively engage the middle section 14 of the surgical staple 10 near the other side section 16. Additionally, as with the previous embodiment, one of the engagement members 432 selectively engages the surgical staple 10 from a front side of the surgical staple 10, and the other engagement member 32 selectively engages the surgical staple 10 from a back side (i.e. the opposite side) of the surgical staple 10. Further, in the embodiment shown in FIG. 4, the engagement members 432 do not engage the side sections 16 of the surgical staple 10.

Additionally, in one embodiment, while the engagement members 432 are engaging the surgical staple 10, the middle section 14 of the surgical staple 10 is further in contact with an end 426 of the inserter body 418. With this design, during use, there are again three points of contact, or pressure points, between the surgical staple 10 and the staple inserter 412. More particularly, in this embodiment, the three points of contact put the middle section 14 of the surgical staple 10 into three-point bending. With the three points of contact as discussed herein, the staple inserter 12 applies pressure at each of these three points of contact to effectively maintain the side sections 16 in the opened configuration such that the side sections 16 can be easily and accurately inserted into the holes in the bone material. Stated another way, the three points of contact between the staple inserter 12 and the surgical staple 10 when the staple inserter 12 is in the attached position enable the surgical staple 10 to be retained in the opened configuration. In particular, the pressure on the middle section 14 from the end 426 of the inserter body 418 tends to maintain the side sections 16 slightly opened or spread apart relative to the relaxed configuration of the surgical staple 10; and the pressure of the engagement members 432 against an inner surface of the middle section 14 also tends to maintain the side sections 16 slightly opened or spread apart relative to the relaxed configuration of the surgical staple 10. This enables the side sections 16 to be more easily, accurately and precisely inserted into the holes in the bone material as desired.

After the surgical staple 10 has been inserted into the holes in the bone material (or otherwise inserted as desired), the staple inserter 412 can be rotated in the second direction, e.g., by rotating the inserter body 418, so that the staple holder assembly 420 (and thus the engagement members 432) becomes disengaged from the surgical staple 10, i.e. so that the staple inserter 412 and/or the engagement members 432 are moved from the attached position to the detached position. At this point the staple inserter 412 can be moved away from the surgical staple 10.

While a number of exemplary aspects and embodiments of a staple inserter 12 have been shown and disclosed herein above, those of skill in the art will recognize certain modifications, permutations, additions and sub-combinations thereof. It is therefore intended that the staple inserter 12 shall be interpreted to include all such modifications, permutations, additions and sub-combinations as are within their true spirit and scope, and no limitations are intended to the details of construction or design herein shown.

What is claimed is:

1. A staple inserter for use with a surgical staple during a surgical procedure, the surgical staple including a middle section and two side sections that cantilever away from the middle section, the surgical staple being selectively movable between a relaxed configuration and an opened configuration, the staple inserter comprising:
   a staple holder assembly that is rotatable in a first direction about a longitudinal axis of the staple inserter, wherein the staple holder assembly is rotatable with respect to the staple inserter to selectively engage and retain the surgical staple, wherein the longitudinal axis of the staple inserter is parallel to the side sections of the surgical staple.

2. The staple inserter of claim 1 wherein the staple holder assembly includes (i) a first engagement member that is rotatable in the first direction about the longitudinal axis to selectively engage and retain the surgical staple, and (ii) a second engagement member that is rotatable in the first direction about the longitudinal axis to selectively engage and retain the surgical staple.

3. The staple inserter of claim 2 wherein the first engagement member engages one of the side sections of the surgical staple, and wherein the second engagement member engages the other side section of the surgical staple.

4. The staple inserter of claim 3 further comprising an inserter body, wherein the staple holder assembly is coupled to the inserter body, and wherein the inserter body includes an end that engages the middle section of the surgical staple when the engagement members are engaging the side sections of the surgical staple.

5. The staple inserter of claim 2 wherein each of the first engagement and the second engagement member engage the middle section of the surgical staple.

6. The staple inserter of claim 5 further comprising an inserter body, wherein the staple holder assembly is coupled to the inserter body, and wherein the inserter body includes an end that engages the middle section of the surgical staple when the engagement members are engaging the middle section of the surgical staple.

7. The staple inserter of claim 1 wherein the staple holder assembly is rotatable relative to the surgical staple about a staple axis to selectively engage and retain the surgical staple, the staple axis being substantially parallel to the side sections when the surgical staple is in the opened configuration.

8. The staple inserter of claim 1 wherein when the staple holder assembly is engaging the surgical staple, the surgical staple is retained in the opened configuration, and wherein when the staple holder assembly is not engaging the surgical staple, the surgical staple is in the relaxed configuration.

9. The staple inserter of claim 1 further comprising an inserter body, wherein the staple holder assembly is coupled to the inserter body.

10. The staple inserter of claim 9 wherein the staple holder assembly is made from a metallic material and the inserter body is made from a plastic material.

11. The staple inserter of claim 1 wherein the staple holder assembly is rotatable in a second direction relative to the surgical staple to disengage from the surgical staple, the second direction being opposite from the first direction.

12. A combination comprising (i) a surgical staple including a middle section and two side sections that cantilever away from the middle section, the surgical staple being selectively movable between a relaxed configuration and an opened configuration, and (ii) the staple inserter of claim 1 that selectively engages and retains the surgical staple.

13. The method of claim 12 further comprising the step of rotating the staple holder assembly in a second direction relative to the surgical staple to disengage from the surgical staple, the second direction being opposite from the first direction.

14. A method for engaging and retaining a surgical staple during a surgical procedure, the surgical staple including a middle section and two side sections that cantilever away from the middle section, the surgical staple being selectively movable between a relaxed configuration and an opened configuration, the method comprising the step of:
rotating a staple holder assembly in a first direction about a longitudinal axis of the staple holder and with respect to the staple inserter to selectively engage and retain the surgical staple, wherein the longitudinal axis of the staple holder is parallel to the side sections of the surgical staple.

15. The method of claim 14 wherein the step of rotating includes (i) rotating a first engagement member in the first direction about the longitudinal axis to selectively engage and retain the surgical staple, and (ii) rotating a second engagement member in the first direction about the longitudinal axis to selectively engage and retain the surgical staple.

16. The method of claim 15 wherein the first engagement member engages at least one of one of the side sections and the middle section of the surgical staple, and wherein the second engagement member engages at least one of the other side section and the middle section of the surgical staple.

17. The method of claim 16 further comprising the steps of coupling the staple holder assembly to an inserter body, and engaging the middle section of the surgical staple with an end of the inserter body when the engagement members are engaging the side sections of the surgical staple.

18. The method of claim 14 wherein the step of rotating includes rotating the staple holder assembly relative to the surgical staple about a staple axis to selectively engage and retain the surgical staple, the staple axis being substantially parallel to the side sections when the surgical staple is in the opened configuration.

19. The method of claim 14 wherein when the staple holder assembly is engaging the surgical staple, the surgical staple is retained in the opened configuration, and wherein when the staple holder assembly is not engaging the surgical staple, the surgical staple is in the relaxed configuration.

20. A staple inserter for use with a surgical staple during a surgical procedure, the surgical staple including a middle section and two side sections that cantilever away from the middle section, the surgical staple being selectively movable between a relaxed configuration and an opened configuration, the staple inserter comprising:
a first inserter member that selectively engages the surgical staple when the surgical staple is in the opened configuration, the first inserter member being made from a metallic material, wherein the first inserter member is rotatable in a first direction about a longitudinal axis of the staple inserter and with respect to the staple inserter to selectively engage and retain the surgical staple, wherein the longitudinal axis of the staple inserter is parallel to the side sections of the surgical staple; and
a second inserter member that is coupled to the first inserter member, the second inserter member selectively engaging the surgical staple when the surgical staple is in the opened configuration, the second inserter member being made from a plastic material.

21. The staple inserter of claim 20 wherein second inserter member is rotatable in the first direction about the longitudinal axis to selectively engage and retain the surgical staple.

22. The staple inserter of claim 21 wherein the first inserter member includes (i) a first engagement member that is rotatable in the first direction about the longitudinal axis to selectively engage at least one of one of the side sections and the middle section of the surgical staple, and (ii) a second engagement member that is rotatable in the first direction about the longitudinal axis to selectively engage at least one of the other side section and the middle section of the surgical staple; and wherein the second inserter member includes an end that engages the middle section of the surgical staple when the engagement members are engaging the surgical staple.

* * * * *